(12) United States Patent
Russell et al.

(10) Patent No.: US 9,691,253 B2
(45) Date of Patent: Jun. 27, 2017

(54) PREVENTING FALLS USING POSTURE AND MOVEMENT DETECTION

(71) Applicant: Covidien LP, Mansfield, MA (US)

(72) Inventors: Brian Keith Russell, Annapolis, MD (US); Jonathan James Woodward, Annapolis, MD (US); Dietrich Otto Ruehlmann, Gaithersburg, MD (US); Marjorie Jones Olsen, Charlotte, NC (US); Benjamin David Morris, Annapolis, MD (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/611,893

(22) Filed: Feb. 2, 2015

(65) Prior Publication Data

US 2015/0221202 A1 Aug. 6, 2015

Related U.S. Application Data

(60) Provisional application No. 61/935,581, filed on Feb. 4, 2014.

(51) Int. Cl.
*G08B 23/00* (2006.01)
*G08B 21/04* (2006.01)
*A61B 5/00* (2006.01)
*A61B 5/11* (2006.01)

(52) U.S. Cl.
CPC .......... *G08B 21/0446* (2013.01); *A61B 5/002* (2013.01); *A61B 5/1117* (2013.01); *A61B 5/1118* (2013.01); *G08B 21/043* (2013.01)

(58) Field of Classification Search
CPC .............. G08B 21/0446; G08B 21/043; G06F 19/3418; A61B 5/0022; A61B 5/0002; A61B 5/021; A61B 5/0205; A61B 5/002; A61B 5/1118; A61B 5/747; A61B 5/1112; A61B 5/1116; A61B 5/02438; A61B 5/0024; A61B 5/7228
USPC ...................................................... 340/573.7
See application file for complete search history.

(56) References Cited

U.S. PATENT DOCUMENTS

| 6,389,072 B1 * | 5/2002 | Tzou ................... H04N 19/197 348/699 |
| 7,978,062 B2 * | 7/2011 | LaLonde ............ A61N 1/37282 340/539.1 |
| 2004/0145493 A1 * | 7/2004 | O'Connor ............ A61B 5/6828 340/870.09 |

(Continued)

OTHER PUBLICATIONS

International Search Report for International application No. PCT/US2015/014214 mailed May 15, 2015 from Korean Intellectual Property Office.

*Primary Examiner* — Qutbuddin Ghulamali

(57) ABSTRACT

Methods, apparatuses and systems are described for associating remote physiological monitoring with an at-risk falling condition of a patient. The methods may include receiving movement data of a patient from one or more sensors. The methods may also include determining a patient posture and a patient activity level based, at least in part, on the received movement data, and determining that an at-risk condition is satisfied by the patient posture or the patient activity level. Once it is determined that the at-risk condition is satisfied, the methods may also include issuing an alert based, at least in part, on the determination that the at-risk condition is satisfied.

20 Claims, 9 Drawing Sheets

(56) References Cited

U.S. PATENT DOCUMENTS

| | | |
|---|---|---|
| 2008/0238692 A1* | 10/2008 | Dayton .................... G07C 3/00 340/573.1 |
| 2008/0272918 A1 | 11/2008 | Ingersoll |
| 2008/0275349 A1 | 11/2008 | Halperin et al. |
| 2010/0298661 A1 | 11/2010 | McCombie et al. |
| 2012/0092156 A1 | 4/2012 | Tran |
| 2013/0030825 A1 | 1/2013 | Bagwandeen et al. |

* cited by examiner

PREVENTING FALLS USING POSTURE AND MOVEMENT DETECTION

CROSS-REFERENCE TO RELATED APPLICATIONS

This application claims priority to U.S. Provisional Patent Application No. 61/935,581 filed on Feb. 4, 2014, the entirety of which is incorporated by reference herein.

BACKGROUND

The present disclosure relates generally to patient monitoring systems, and more particularly to preventing falls by detecting patient movement data associated with patient posture and activity levels.

Patients having physical disabilities, or who have recently undergone surgical procedures, may not have the strength or coordination to safely exit their beds without assistance due to compromised strength, stamina, coordination, etc. Such individuals, however, may occasionally attempt to get out of bed and walk around without assistance because they believe that they can do so safely or because they fail to understand their physical limitations. There may be a high risk of injury to these individuals if they attempt to exit their beds when it is not safe to do so.

Some hospitals or care facilities employ "sitters" to remain in the room with the patient at all times to ensure that the patient does not attempt to exit the bed without assistance. However, hiring sitters can be costly for already understaffed healthcare centers. Other systems may include physically tethering patients to their beds, but such methods may be excessively restrictive for patients in the long term.

Other known methods may monitor an individual in bed using, for example, bed-based pressure sensors and/or video monitoring. Pressure sensors may detect when a user leaves the bed, but, at that point, it may be too late to prevent the patient from falling and sustaining an injury. Video monitoring may employ virtual gating to detect the patient's movement out of the bed, but is often subject to false positives, for example when the patient reaches across the virtual gate to grab a glass of water, thereby triggering an alert falsely indicating that the patient has left or is attempting to leave the bed.

Therefore, improvements in remote monitoring of bed-ridden patients may be beneficial.

SUMMARY

In some instances, a patient may sit up and put his legs over the side of the bed prior to standing and exiting the bed, while in other instances, the patient may simply roll or slide off the side of the bed without first sitting up. It may therefore be beneficial to monitor two separate parameters that may indicate that the patient is at risk of falling. One method of accomplishing this may include receiving movement data of a patient from one or more sensors, and determining a patient posture and a patient activity level based, at least in part, on the received movement data. The method may then include determining that an at-risk condition is satisfied by the patient posture or the patient activity level. An alert may be issued based, at least in part, on the determination that the at-risk condition is satisfied.

By collecting patient movement data and determining one or both of a patient posture and a patient activity level in order to determine that an at-risk condition is satisfied, a patient may be determined to be at risk of falling under a variety of circumstances. For example, where a patient has sat up and is attempting to rise into a standing position, the patient may be determined to be at-risk. In addition or alternatively, where a patient has not sat up, but has increased his activity level by rolling or shifting toward the edge of the bed in an attempt to exit the bed, the patient may also be determined to be at risk of falling. Thus, a variety of at-risk scenarios may be monitored and may trigger alerts, such that potential patient falls may be prevented.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label with a dash and a second label that distinguishes among the similar components. If only the first reference label is used in the specification, the description is applicable to any one of the similar components having the same first reference label irrespective of the second reference label.

DETAILED DESCRIPTION

In order to effectively prevent injuries resulting from falls when patients who are not sufficiently physically strong or coordinated attempt to leave their beds without assistance, a caregiver may benefit from prior notice or warning that the patients are attempting to leave their beds. Yet, without being physically in the room or in line of sight with the patients, it may be difficult or impossible for the caregiver to continuously monitor the patients' movements. Thus, it may be desirable to remotely monitor a patient's movements in his or her bed that may indicate a patient's attempt at exiting the bed. This attempt may be measured by monitoring when the patient has moved from a supine or reclined position to an upright position, or by detecting an increase in patient activity levels, or both. When one or both of these conditions meets or surpasses a predetermined threshold, it may be determined that the patient is at risk for falling, and a caregiver may be alerted such that he or she may go to the patient and either prevent or assist the patient in getting out of bed.

In order to avoid false alarms, it may be desirable to provide a means by which minor patient movements, like reaching for water, sitting up briefly to readjust pillows, or the like, may be disregarded as mere "glitches" not indicative of a true at-risk status of the patient. Thus, a posture timer and/or an activity timer may be operated to measure the patient's posture or activity level for a predetermined period of time during which the at-risk condition is satisfied, and to issue an alert when the posture timer and/or activity timer meets or surpasses a predetermined threshold. In this way, a patient who has sat up but who has no intention to leave the bed and instead quickly lies back down, may not trigger unnecessary alerts for caregivers busy with other patients.

The present disclosure includes a method and system for preventing falls using monitored patient posture and activity level data. The patient posture and patient activity level may be derived based, at least in part, on received movement data of the patient. One example of a patient movement monitoring system is a remote patient movement monitoring system. Examples below describe such a system, though it should be understood that any type of patient movement monitoring system may provide patient posture data and patient activity data from which an at-risk status may be determined for issuing an alert to a caregiver.

Figure 1:
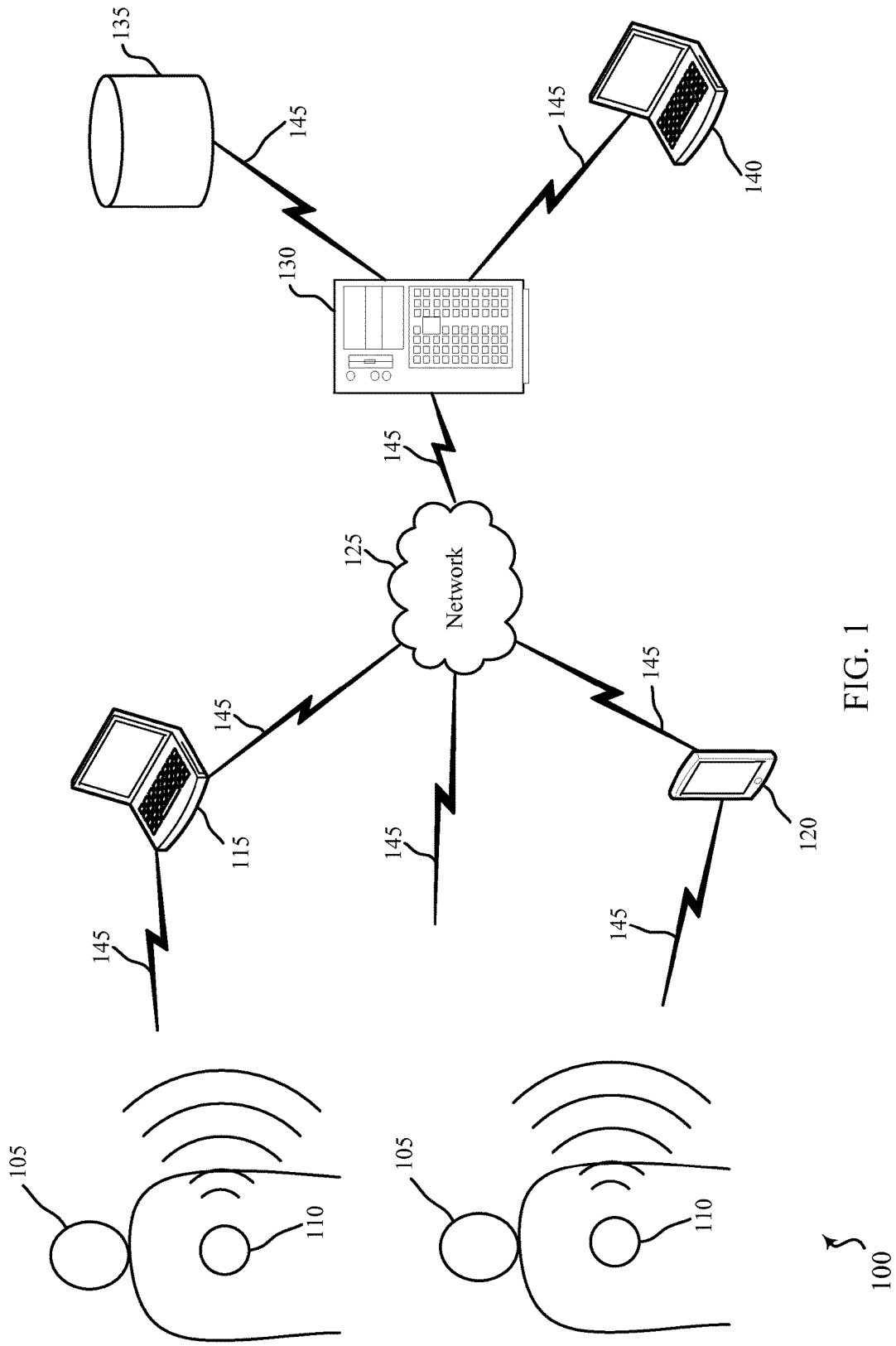
FIG. 1 is a block diagram of an example of a patient movement monitoring system in accordance with various embodiments.

Referring first to FIG. 1, a diagram illustrates an example of a remote patient movement monitoring system 100. The system 100 includes patients 105, each wearing a sensor unit 110. The sensor units 110 may transmit signals via wireless communication links 145. The transmitted signals may be transmitted to local computing devices 115, 120. Local computing device 115 may be a local caregiver's station, for example. Local computing device 120 may be a mobile device, for example. The local computing devices 115, 120 may be in communication with a server 130 via network 125. The sensor units 110 may also communicate directly with the server 130 via the network 125. The server 130 may be in further communication with a remote computing device 140, thus allowing a caregiver to remotely monitor the patients 105. The server 130 may also be in communication with various medical databases 135 where the collected data may be stored.

The sensor units 110 are described in greater detail below. The sensor units 110 may be a body-worn device, coupled to the patient's chest or to any other suitable portion of the patient's body, such as the patient's arm, wrist, or thigh. The sensor units 110 may be coupled to the patient using an adhesive, a strap, or any other suitable means. In an alternative embodiment, the sensor units 110 may be coupled to or integral with a garment worn by a patient, such as a belt, wristband, headband, armband, or piece of clothing.

In some embodiments, the sensor units 110 are sensors configured to conduct periodic or ongoing automatic measurements of one or more patient movement data parameters. A patient may wear or otherwise be attached to one or more sensor units 110 so that the sensor units 110 may measure, record, and/or report patient movement measurements.

Each sensor unit 110 may be capable of sensing multiple patient movement measurements, as well as sensing patient posture and patient activity level data. Thus, the sensor units 110 may each include multiple sensors such as accelerometers, gyroscopes, and position sensors. For example, a first sensor in a sensor unit 110 may be a single- or multiple-axis accelerometer, such as a microelectromechanical system (MEMS) accelerometer, a piezoelectric accelerometer, or a mechanical accelerometer. A second sensor within a sensor unit 110 may be operable to detect patient position. For example, the second sensor may include a gyroscope and/or a position sensor operable to detect orientation, angular position, angular velocity, and/or angular acceleration of the sensor unit 110, and by extension, of the patient 105. Multiple sensor units 110 may be used on a single patient 105. The data collected by the sensor units 110 may be wirelessly conveyed to either the local computing devices 115, 120 or to the remote computing device 140 (via the network 125 and server 130). Data transmission may occur via, for example, frequencies appropriate for a personal area network (such as Bluetooth or IR communications) or local or wide area network frequencies such as radio frequencies specified by the IEEE 802.15.4 standard.

The sensor units 110 may additionally include additional inputs from, for example, external devices such as pressure pads, camera movement detectors, radars, wireless movement detectors, and the like. In other embodiments, the sensor units 110 may include one or more detectors and/or sensors operable to detect any of heart rate, blood pressure, respiratory rate, and/or any other suitable physiological parameters, as illustrated and described in U.S. Patent Publication No. 2011/0257542, filed Apr. 15, 2011; U.S. Patent Publication No. 2012/0143019, filed Jun. 6, 2011; U.S. Patent Publication No. 2009/0227856, filed Dec. 19, 2008; U.S. Patent Publication No. 2009/0281394, filed Sep. 21, 2007; U.S. Patent Publication No. 2013/0144130, filed Jan. 30, 2012; U.S. Patent Application No. 61/823,596, filed Mar. 15, 2013; U.S. Patent Application No. 61/864,161, filed Aug. 9, 2013; U.S. Pat. No. 8,400,302, issued Mar. 19, 2013; and/or U.S. Pat. No. 8,079,247, issued Dec. 20, 2011, each of which is commonly owned and which is incorporated herein by reference in its entirety.

In one embodiment, one or more sensor units 110 comprises an accelerometer to measure patient activity data. The accelerometer may be a three-axis MEMS accelerometer, a piezoelectric accelerometer, a mechanical accelerometer, and/or any other suitable device to detect acceleration and/or static acceleration fields (e.g., the gravitational field). In addition or alternatively, the accelerometer may include a gyroscope operable to detect angular position, angular velocity, and/or angular acceleration of the sensor unit 110.

The local computing devices 115, 120 may enable the patient 105 and/or a local caregiver to monitor the collected patient movement data measurements. For example, the local computing devices 115, 120 may be operable to present data collected from sensor units 110 in a human-readable format. For example, the received data may be outputted as a display on a computer or a mobile device. The local computing devices 115, 120 may include a processor that may be operable to present data received from the sensor units 110 in a visual format. The local computing devices 115, 120 may also output data in an audible format using, for example, a speaker. In alternative embodiments, the received data may be outputted as a display or in an audible format from the one or more sensor units 110 themselves.

The local computing devices 115, 120 may be custom computing entities configured to interact with the sensor units 110. In some embodiments, the local computing devices 115, 120 and the sensor units 110 may be portions of a single sensing unit operable to sense and display patient movement measurements. In another embodiment, the local computing devices 115, 120 may be general purpose computing entities such as a personal computing device, for example a desktop computer, a laptop computer, a netbook, a tablet personal computer (PC), an iPod®, an iPad®, a smartphone (e.g., an iPhone®, an Android® phone, a Blackberry®, a Windows® phone, etc.), a mobile phone, a personal digital assistant (PDA), and/or any other suitable device operable to send and receive signals, store and retrieve data, and/or execute modules.

The local computing devices 115, 120 may include memory, a processor, an output, a data input and a communication module. The processor may be a general purpose processor, a Field Programmable Gate Array (FPGA), an Application Specific Integrated Circuit (ASIC), a Digital Signal Processor (DSP), and/or the like. The processor may be configured to retrieve data from and/or write data to the memory. The memory may be, for example, a random access memory (RAM), a memory buffer, a hard drive, a database, an erasable programmable read only memory (EPROM), an electrically erasable programmable read only memory (EEPROM), a read only memory (ROM), a flash memory, a hard disk, a floppy disk, cloud storage, and/or so forth. In some embodiments, the local computing devices 115, 120 may include one or more hardware-based modules (e.g., DSP, FPGA, ASIC) and/or software-based modules (e.g., a module of computer code stored at the memory and executed at the processor, a set of processor-readable instructions that may be stored at the memory and executed at the processor) associated with executing an application, such as, for example, receiving and displaying data from sensor units 110.

The data input module of the local computing devices 115, 120 may be used to manually input patient movement data instead of or in addition to receiving data from the sensor units 110. For example, a user of the local computing device 115, 120 may make an observation as to the posture and/or activity level of a patient and record the observation using the data input module. A user may be, for example, a nurse, a doctor, and/or any other medical healthcare professional authorized to record patient observations, the patient, and/or any other suitable person. For instance, the user may observe that the patient is in a supine position, and may input that data into the data input module. In some embodiments, the data input module may be operable to allow the user to select "patient posture" and input the observed patient posture into the data input module, e.g., using a keyboard. In other embodiments, the data input module may be operable to allow the user to select whether the patient is stationary or is mechanically in motion.

The processor of the local computing devices 115, 120 may be operated to control operation of the output of the local computing devices 115, 120. The output may be a television, liquid crystal display (LCD) monitor, cathode ray tube (CRT) monitor, speaker, tactile output device, and/or the like. In some embodiments, the output may be an integral component of the local computing devices 115, 120. Similarly stated, the output may be directly coupled to the processor. For example, the output may be the integral display of a tablet and/or smartphone. In some embodiments, an output module may include, for example, a High Definition Multimedia Interface™ (HDMI) connector, a Video Graphics Array (VGA) connector, a Universal Serial Bus™ (USB) connector, a tip, ring, sleeve (TRS) connector, and/or any other suitable connector operable to couple the local computing devices 115, 120 to the output.

As described in additional detail herein, at least one of the sensor units 110 may be operable to transmit patient movement measurements to the local computing devices 115, 120 and/or to the remote computing device 140 continuously, at scheduled intervals, when requested, and/or when certain conditions are satisfied (e.g., during an at-risk condition). In some embodiments, the rate at which patient movement measurements are collected and/or transmitted may increase when the patient is determined to be at-risk.

The remote computing device 140 may be a computing entity operable to enable a remote user to monitor the output of the sensor units 110. The remote computing device 140 may be functionally and/or structurally similar to the local computing devices 115, 120 and may be operable to receive data streams from and/or send signals to at least one of the sensor units 110 via the network 125. The network 125 may be the Internet, an intranet, a personal area network, a local area network (LAN), a wide area network (WAN), a virtual network, a telecommunications network implemented as a wired network and/or wireless network, etc. The remote computing device 140 may receive and/or send signals over the network 125 via communication links 145 and server 130.

The remote computing device 140 may be used by, for example, a health care professional to monitor the output of the sensor units 110. In some embodiments, the remote computing device 140 may receive an indication of patient movement measurements when the sensors detect an at-risk condition, when the healthcare provider requests the information, at scheduled intervals, and/or at the request of the healthcare provider and/or the patient 105. For example, the remote computing device 140 may be operable to receive summarized patient movement measurements from the server 130 and display the summarized patient movement measurements in a convenient format. The remote computing device 140 may be located, for example, at a nurses' station or in a patient's room, and may be configured to display a summary of the patient movement measurements collected from one or more patients. In some instances, the local computing devices 115, 120 may also be operable to receive and display patient movement measurements in much the same way that the remote computing device 140 is operable.

The server 130 may be configured to communicate with the sensor units 110, the local computing devices 115, 120, the remote computing device 140, and databases 135. The server 130 may perform additional processing on signals received from the sensor units 110 or local computing devices 115, 120, or may simply forward the received information to the remote computing device 140 and databases 135. The databases 135 may be examples of electronic health records ("EHRs") and/or personal health records ("PHRs"), and may be provided by various service providers. In certain embodiments, the server 130 may be combined with one or more of the local computing devices 115, 120 and/or the remote computing device 140.

The server 130 may be a computing device operable to receive data streams (e.g., from the sensor units 110 and/or the local computing devices 115, 120), store and/or process data, and/or transmit data and/or data summaries (e.g., to the remote computing device 140). For example, the server 130 may receive a stream of patient posture data from a sensor unit 110, and a stream of patient activity level data from the same or a different sensor unit 110. Based on one or both of the posture data and activity level data received, the server 130 may be able to determine whether the patient is at risk of falling, and may issue an alert accordingly. In some embodiments, the server 130 may "pull" the data streams, e.g., by querying the sensor units 110 and/or the local computing devices 115, 120. In some embodiments, the data streams may be "pushed" from the sensor units 110 and/or the local computing devices 115, 120 to the server 130. For example, the sensor units 110 and/or the local computing devices 115, 120 may be configured to transmit data as it is generated by or entered into that device. In some instances, the sensor units 110 and/or the local computing devices 115, 120 may periodically transmit data (e.g., as a block of data or as one or more data points).

The server 130 may include a database (e.g., in memory) containing patient movement data received from the sensor units 110 and/or the local computing devices 115, 120. Additionally, as described in further detail herein, software (e.g., stored in memory) may be executed on a processor of the server 130. Such software (executed on the processor) may be operable to cause the server 130 to monitor, process, summarize, present, and/or send a signal associated with patient movement measurements.

Although the server 130 and the remote computing device 140 are shown and described as separate computing devices, in some embodiments, the remote computing device 140 may perform the functions of the server 130 such that a separate server 130 may not be necessary. In such an embodiment, the remote computing device 140 may receive patient movement data streams from the sensor units 110 and/or the local computing devices 115, 120, process the received patient movement data, and display the processed data as summarized patient movement data, with at-risk flags associated with patient movement data that has exceeded predetermined thresholds.

Additionally, although the remote computing device 140 and the local computing devices 115, 120 are shown and described as separate computing devices, in some embodiments, the remote computing device 140 may perform the functions of the local computing devices 115, 120 such that a separate local computing device 115, 120 may not be necessary. In such an embodiment, the user (e.g., a nurse or a doctor) may manually enter the patient's movement data (e.g., the patient's activity level) directly into the remote computing device 140.

In the system 100 of FIG. 1, a sensor unit 110 may detect movement data of the patient 105. In some embodiments, a single sensor unit 110 may detect both patient posture and patient activity level data. In alternate embodiments, one sensor unit 110 may detect patient posture, while a second sensor unit 110 may detect patient activity level data. Activity data received by sensor unit 110 may comprise any one or more of position, velocity, or acceleration data. Patient posture data may indicate the orientation of the sensor 110, and by extension, of the patient 105, with respect to a horizontal plane.

Based on the received activity data and/or patient posture data, it may be determined that the patient is at risk of falling. This determination may be made at the one or more sensor units 110, or may be determined at any one of the local computing devices 115, 120, the remote computing device 140, and/or the server 130. Patient movement measurements may be received on an ongoing basis from the one or more sensor units 110. Upon determining that the patient is at risk of falling, an alert may be issued, notifying the caregiver that the patient is in danger. This "at-risk flag" may be transmitted to the patient or clinician to be displayed, for example, at a nurses' station or in a patient's room, or alternatively on any of the local computing devices 115, 120 or the remote computing device 140.

Figure 2:
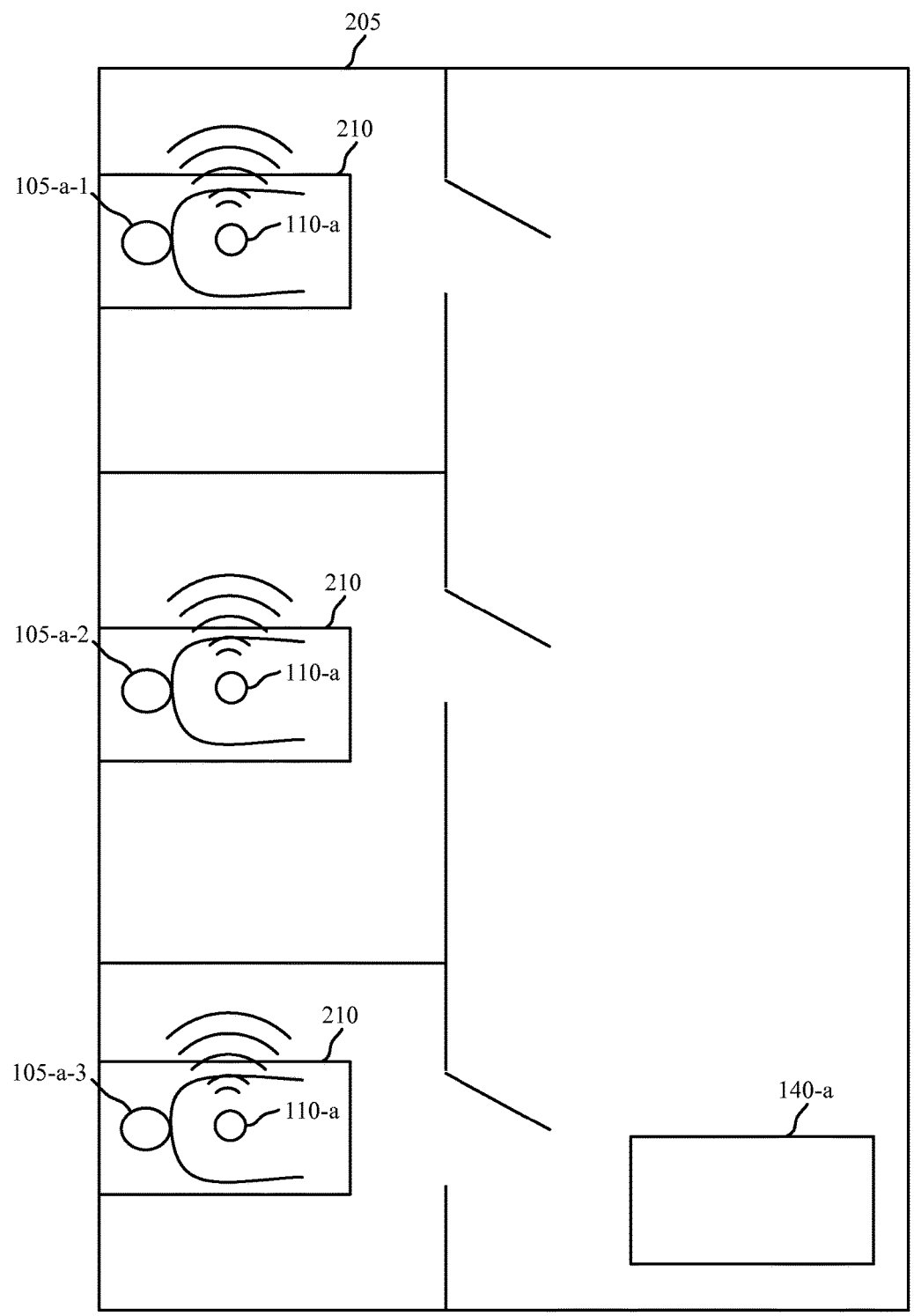
FIG. 2 is a block diagram of an example of a patient movement monitoring system in a healthcare facility environment, in accordance with various embodiments.

FIG. 2 is a block diagram 200 showing a top-down configuration of sensor units 110-a and patients 105-a-1, 105-a-2, 105-a-3 in a hospital space, according to one embodiment. Where a patient has recently undergone a surgical procedure, or is otherwise too weak or unstable to safely exit his bed without assistance, it may be necessary to provide constant monitoring of the patient to ensure that he does not attempt to get out of bed. Yet, with many hospitals being understaffed, or where some patients may be recovering at home, it may not be feasible to provide continuous, in-person monitoring. Accordingly, it may be advantageous to provide a means by which a single caregiver, for example positioned at a nurses' station or other remote computing device 140-a, may monitor a plurality of patients 105-a-1, 105-a-2, 105-a-3 all at once, without being within line of sight of any or all of the patients 105-a-1, 105-a-2, 105-a-3. In one embodiment, each of the patients 105-a-1, 105-a-2, 105-a-3 may be positioned on separate hospital beds 210 in separate rooms of the hospital or care facility 205. A sensor unit 110-a may be coupled to each patient 105-a-1, 105-a-2, 105-a-3, or may alternatively be integrated with a garment worn by each patient 105-a-1, 105-a-2, 105-a-3. Each sensor unit 110-a may be configured to monitor movement data of each patient, where the movement data may be utilized to determine one or more of a patient posture and a patient activity level. For example, an acceleration signal received by the sensor unit 110-a may be processed to derive the orientation of the sensor unit 110-a with respect to a horizontal plane, based on the direction of the gravitational field. This orientation may then be correlated with the orientation of the patient 105-a-1, 105-a-2, 105-a-3, to determine whether the patient 105-a-1, 105-a-2, 105-a-3 is reclined, sitting, and/or standing. Similarly, the acceleration signal monitored by the sensor unit 110-a may be processed to calculate a magnitude and/or direction of a three-dimensional acceleration vector. This acceleration vector may then be correlated with physical activity of the patient 105-a-1, 105-a-2, 105-a-3. This physical activity may be used to determine whether the patient is making a concerted, deliberate, and/or sustained movement associated with, for example, getting out of bed.

The patient posture and/or patient activity level data received by the sensor units 110-a may either be processed locally at the sensor units 110-a to determine whether the patient is at risk of falling, or may be communicated to the nurses' station 140-a for processing to determine the same. Additionally, the patient posture and/or patient activity level data may be processed at local computing devices 115, 120 or server 130 (illustrated in FIG. 1). Where it is determined, either at the sensor units 110-a or at the nurses' station 140-a, for example, that one or more of the patients 105-a-1, 105-a-2, 105-a-3 is at-risk of falling, an alert may be issued at any one or more of the sensor units 110-a or nurses' station 140-a. The alert may be in the form of an auditory, visual, and/or haptic alarm. In response to the alert, the nurse or other caregiver may go to the patient 105-a-1, 105-a-2, 105-a-3 to either assist or prevent the patient 105-a-1, 105-a-2, 105-a-3 from leaving his bed. In this way, potential falls may be prevented.

Figure 3:
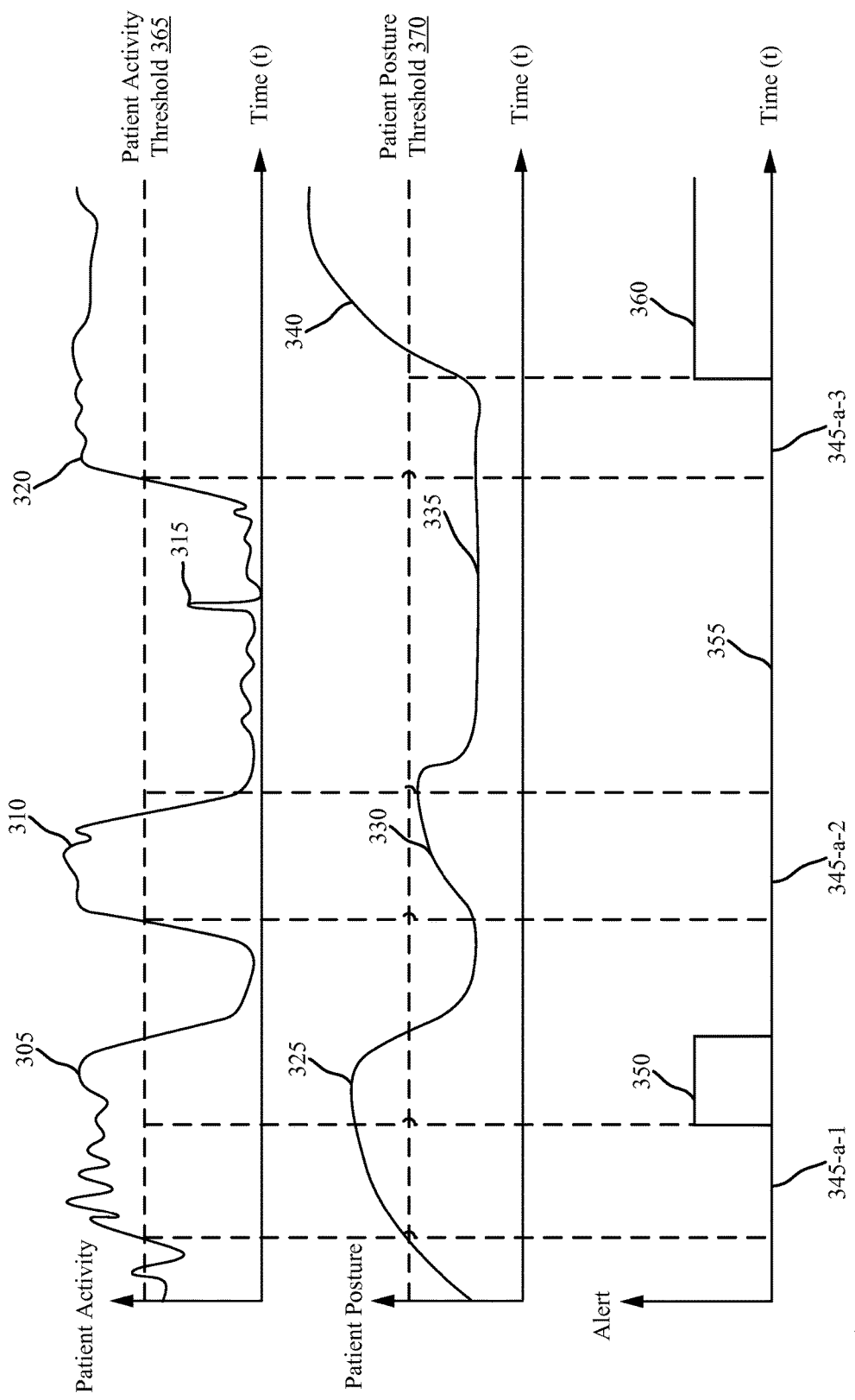
FIG. 3 is a graphical representation of a determination of at-risk status in relation to patient posture data and patient activity data received in accordance with various embodiments.

FIG. 3 is a graphical representation 300 of the collecting of patient activity level and patient posture data, and the determination of an at-risk status for a patient based on the collected data. Patient activity level data and patient posture data may be collected by one or more sensor units 110 as shown in FIG. 1 or 2. In representation 300, examples of collected patient activity level data is illustrated in the form of a patient activity level 305, 310, 315, 320, and examples of collected patient posture data is illustrated in the form of a patient posture level 325, 330, 335, 340. The collected data is collected over a period of time, t.

As shown in FIG. 3, patient activity level corresponds to the collected activity data. In one embodiment, a raw acceleration signal (not shown) may be received in the form of acceleration along a single axis, and/or as a magnitude of a multi-dimensional acceleration vector. The raw acceleration signal may then be normalized by the sensor unit 110 or a signal processing module 415 (as described in relation to FIG. 4), the local computing devices 115, 120, the server 130, and/or the remote computing device 140 to provide a patient activity level curve. A patient posture may be simultaneously monitored by the same or separate one or more sensor units 110.

Representation 300 also illustrates a patient activity threshold 365 and a patient posture threshold 370. The patient activity threshold 365 may be based upon a metabolic equivalence calculated from acceleration data received by one or more sensor units. The metabolic equivalence may be derived by a vector magnitude module 525, described in more detail below with respect to FIG. 5. For example, the patient activity threshold 365 may be equal to 0.2 vector magnitude units (VMUs), or any other suitable acceleration threshold associated with the individual patient attempting to get out of bed. The patient posture threshold 370 may similarly be based upon acceleration data received by one or more sensor units, and may be indicative of a threshold indicating a transition from a relatively low-risk posture (e.g., supine or reclined) to a relatively high-risk posture (e.g., sitting or standing). Thus, the patient posture threshold 370 may be equal to a particular angle above 0 degrees at which the patient is determined to be in a high-risk posture. Either or both of the patient activity threshold 365 and patient posture threshold 370 may be determined based on individual patient physiological parameters.

In one embodiment, a determination of whether a patient is at risk of falling may be based only on the patient activity level determined by the activity data received. In other embodiments, a determination of whether a patient is at risk of falling may be based only on the patient posture level determined by the acceleration data received. In still other embodiments, a determination of at-risk status may be based on both the patient activity level and the patient posture level. Thus, where the patient activity level has surpassed the patient activity threshold 365, and where the patient posture level has surpassed the patient posture threshold 370, it may be determined that an at-risk condition is satisfied, and an alert may be issued.

In some embodiments, the patient may be determined to be at-risk only when the patient activity level and the patient posture level are both above the patient activity threshold 365 and patient posture threshold 370, respectively, for a predetermined period of time. The predetermined period of time may be measured by an at-risk timer window 345-a-1, 345-a-2, 345-a-3 of any suitable length of time to signify that the patient is at risk of getting out of bed; for example 3 seconds, 5 seconds, 10 seconds, 45 seconds, etc. Individual at-risk timer window durations may be adjusted based on individual patients' health and fitness levels. When an at-risk timer, triggered by the patient activity level and/or the patient posture level exceeding a corresponding patient activity threshold 365 and/or patient posture threshold 370, respectively, has surpassed the at-risk timer window 345-a-1, 345-a-2, 345-a-3, the patient may be determined to be at risk of falling, and an alert 350, 360 may be issued. In other embodiments, the patient may be determined to be at-risk when either of the patient activity level or the patient posture level is above the patient activity threshold 365 or the patient posture threshold 370, respectively.

As shown in one example illustrated in FIG. 3, the patient activity level 310 may exceed the patient activity threshold 365 for a period of time that is less than the at-risk timer window 345-a-2, such that an alert may not be issued. This may occur, for example, where a patient has reached for a glass of water, such that an acceleration signal exceeding the patient activity threshold 365 is received, yet the patient has returned to a sedentary state prior to completion of the 10 second at-risk timer window 345-a-2, such that no alert need be provided to indicate that the patient is attempting to get out of bed. In addition, the patient's posture 330 may not have exceeded the patient posture threshold 370, perhaps because the patient may have reached forward or to the side for the glass, without actually coming to a seated position. In another example, a patient may initiate some activity at a level 315 that is less than the patient activity threshold 365, such that an alert is similarly not issued 355. For example, the patient may have reached his hand up to scratch his head, which may result in an acceleration signal that is negligibly small and therefore not indicative of an attempt to exit the bed.

In another example, a patient activity level 305 and patient posture 325 may have both exceeded the patient activity threshold 365 and patient posture threshold 370, respectively. The patient may have maintained each of the patient activity level 305 and the patient posture 325 beyond the span of the at-risk timer window 345-a-1, such that an alert 350 is issued, indicating to the patient and/or caregiver that the patient is attempting to get out of bed and is at risk of falling. Where either or both of the patient activity level and patient posture dip back below the patient activity threshold 365 and patient posture threshold 370, respectively, the alarm or alert 350 may be discontinued. For example, the caregiver may have responded to the alert 350, and may have assisted the patient in lying back down in the bed, such that the patient is no longer at-risk.

In still another example, a patient activity level 320 may have exceeded the patient activity threshold 365, while the patient posture 335 has remained below the patient posture threshold 370. The patient may have maintained the patient activity level 320 beyond the at-risk timer window 345-a-3, such that an alert 360 may be issued, regardless of whether the the patient posture 335 has remained below the patient posture threshold 370. For example, the patient may have begun to roll off the bed, without sitting up from a low-risk supine position to a high-risk seated position. The patient may then transition to a high-risk position 340, while still maintaining a high patient activity level 320, such that the alert 360 may continue to issue, notifying the caregiver that the patient is at risk of falling.

Figure 4:
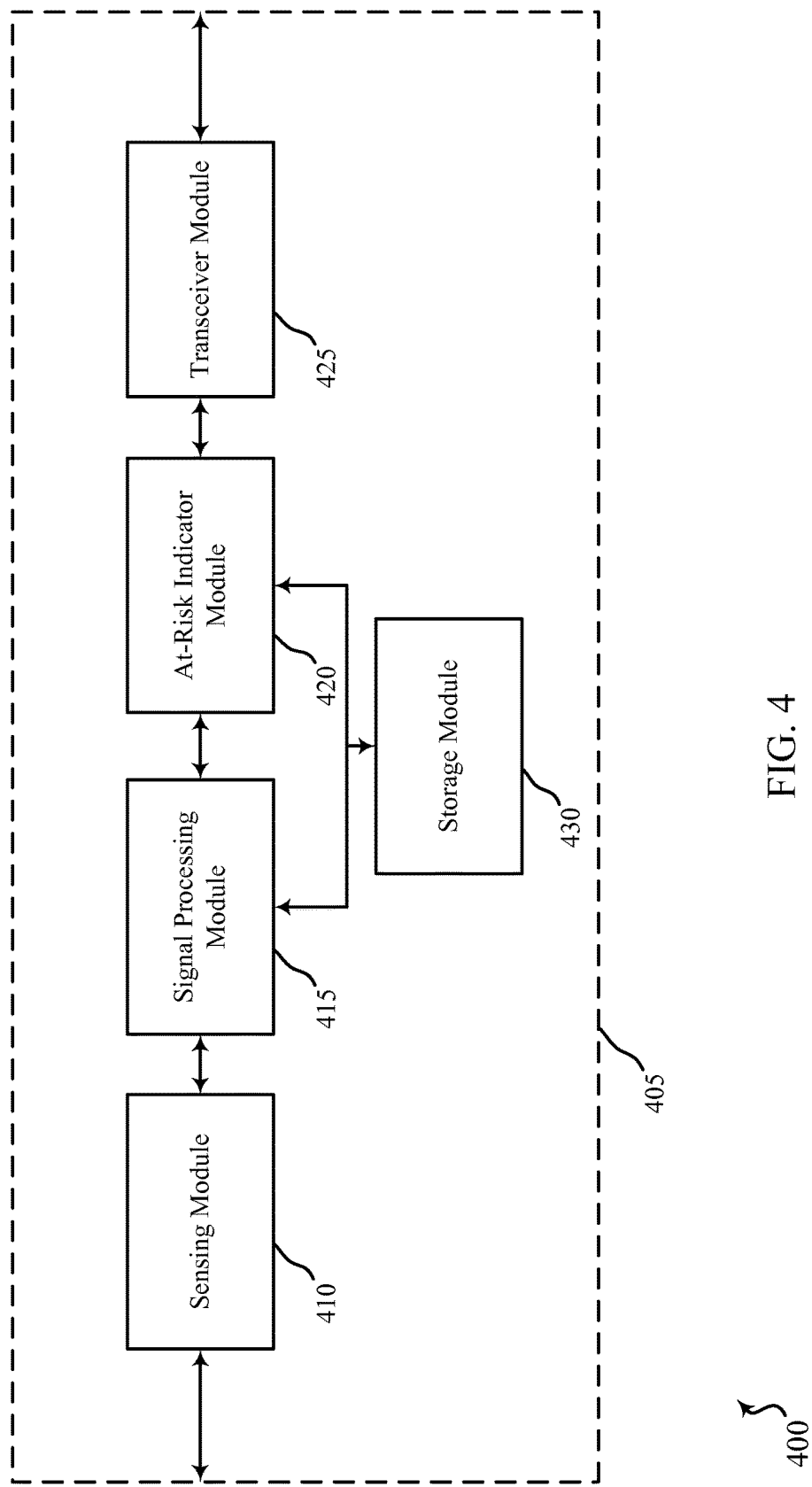
FIG. 4 is a block diagram of an example of an apparatus in accordance with various embodiments.

FIG. 4 shows a block diagram 400 that includes apparatus 405, which may be an example of one or more aspects of the local computing devices 115, 120 and/or remote computing device 140, or may alternatively be an example of one or more aspects of the one or more sensor units 110 (of FIG. 1 or 2), for use in patient movement monitoring, in accordance with various aspects of the present disclosure. In some examples, the apparatus 405 may include a sensing module 410, a signal processing module 415, an at-risk indicator module 420, a transceiver module 425, and a storage module 430. Each of these components may be in communication with each other.

The components of the apparatus 405 may, individually or collectively, be implemented using one or more ASICs adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, FPGAs, and other Semi-Custom ICs), which may be programmed in any manner known in the art. The functions of each unit may also be implemented, in whole or in part, with instructions embodied in a memory, formatted to be executed by one or more general or application-specific processors.

The at-risk indicator module 420 may be configured to monitor the patient movement data sensed by the sensing module 410 and processed by the signal processing module 415, described in more detail below with respect to FIG. 5. In some examples, the at-risk indicator module 420 may determine that the patient is at-risk based, at least in part, on the determination that a patient posture has exceeded a patient posture threshold, and/or that a patient activity level has exceeded a patient activity level threshold. On the basis of this determination that the patient is at-risk, an alert may be issued.

In some examples where apparatus 405 is part of one or more of the local computing devices 115, 120 or remote computing device 140, the transceiver module 425 may be operable to receive data streams from the one or more sensor units 110, as well as to send and/or receive other signals between the sensor units 110 and either the local computing devices 115, 120 or the remote computing device 140 via the network 125 and server 130. In one embodiment, the transceiver module 425 may receive data streams from the sensor units 110 and also forward the data streams to other devices. The transceiver module 425 may include wired and/or wireless connectors. For example, in some embodiments, sensor units 110 may be portions of a wired or wireless sensor network, and may communicate with the local computing devices 115, 120 and/or remote computing device 140 using either a wired or wireless network. The transceiver module 425 may be a wireless network interface controller ("NIC"), Bluetooth® controller, IR communication controller, ZigBee® controller and/or the like.

The local computing device 115, 120 and/or remote computing device 140, upon receiving a signal from the transceiver module 425, may send alerts using such methods as short message service (SMS) text messages, email, or any other suitable means. In embodiments where apparatus 405 is part of one or more of the sensor units 110, transceiver module 425 may send a signal to the local computing device 115, 120 and/or remote computing device 140. In alternative embodiments, where apparatus 405 is part of one or more of the local computing device 115, 120 or remote computing device 140, the transceiver module 425 may communicate the signal within the apparatus 405. For example, if the signal indicates that a patient posture exceeds a threshold, the monitoring station may send information to the patient, a clinician, support personnel, a family member, etc. The information may include an alert, notifying the patient or caregiver that the patient is at risk of falling.

In some embodiments, where apparatus 405 is part of one or more of the sensor units 110, transceiver module 425 may be operable to determine when a local computing device 115, 120 and/or remote computing device 140 is available to receive a signal from the transceiver module 425. For example, the transceiver module 425 may detect when a local computing device 115, 120 and/or remote computing device 140 is within a certain distance of the apparatus 405. In such an embodiment, the transceiver module 425 may push data to the local computing device 115, 120 and/or remote computing device 140. In other embodiments, patient movement data may be pulled from the transceiver module 425 by the local computing device 115, 120 and/or remote computing device 140. In other words, the transceiver module 425 may receive a signal requesting patient movement measurements from the local computing device 115, 120 and/or remote computing device 140.

In some examples, where apparatus 405 is part of one or more of the local computing device 115, 120 or remote computing device 140, or alternatively where apparatus 405 is part of one or more of the sensor units 110, the signal processing module 415 may include circuitry, logic, hardware and/or software for processing the data streams received from the sensor units 110. The signal processing module 415 may include filters, analog-to-digital converters and other digital signal processing units. Data processed by the signal processing module 415 may be stored in a buffer, for example, in the storage module 430. The storage module 430 may include magnetic, optical or solid-state memory options for storing data processed by the signal processing module 415. The at-risk indicator module 420 may access the data stored in the storage module 430 and output an at-risk indicator associated with the patient movement measurements.

Figure 5:
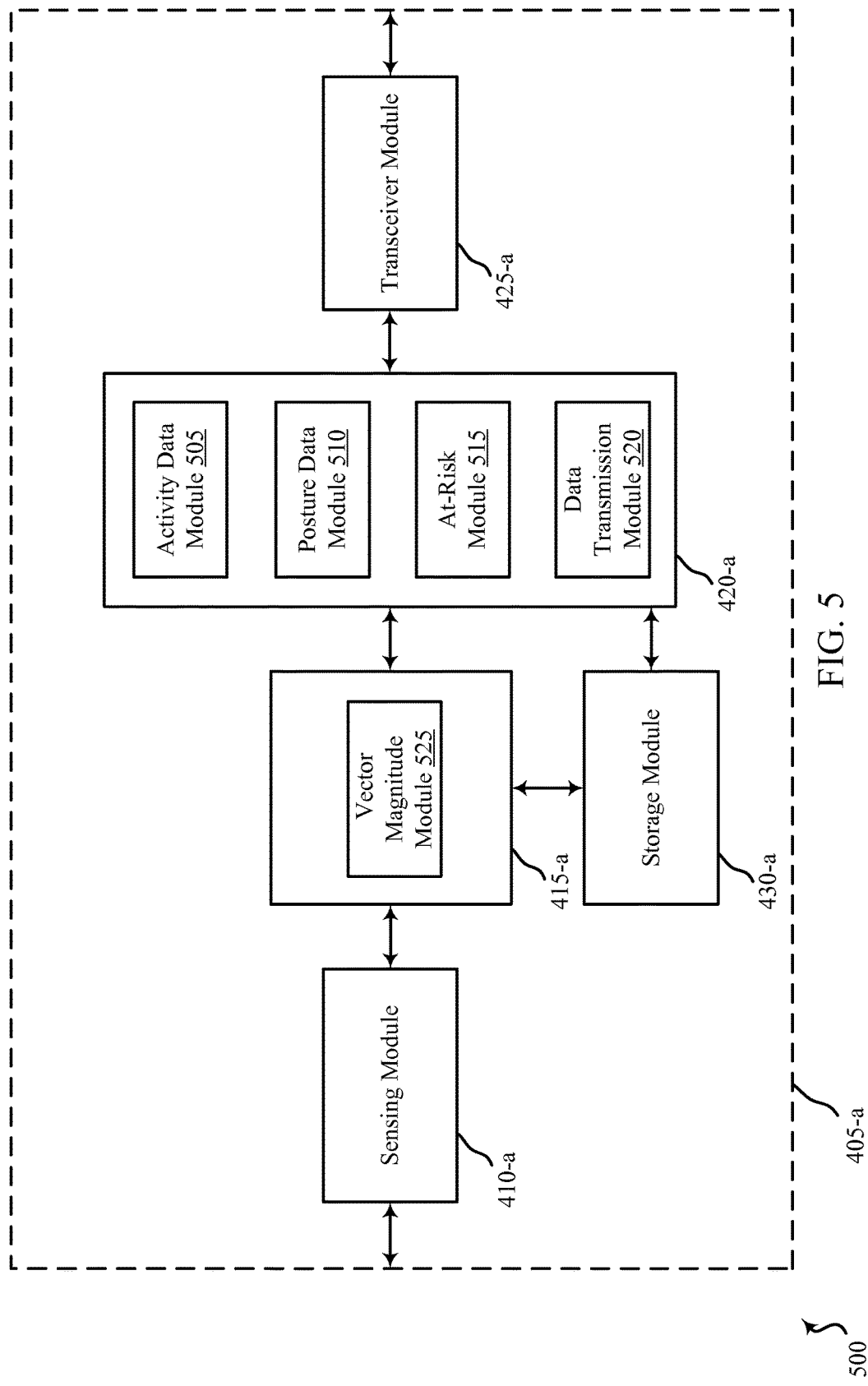
FIG. 5 is a block diagram of an example of an apparatus in accordance with various embodiments.

FIG. 5 shows a block diagram 500 that includes apparatus 405-*a*, which may be an example of apparatus 405 (as illustrated in FIG. 4), in accordance with various aspects of the present disclosure. In some embodiments, apparatus 405-*a* may be part of one or more of the local computing device 115, 120 or remote computing device 140; in alternate embodiments, apparatus 405-*a* may be part of one or more of the sensor units 110. In some examples, the apparatus 405-*a* may include a sensing module 410-*a*, a signal processing module 415-*a*, an at-risk indicator module 420-*a*, a transceiver module 425-*a*, and a storage module 430-*a*, which may be examples of the sensing module 410, signal processing module 415, at-risk indicator module 420, transceiver module 425, and storage module 430 of FIG. 4, respectively. In some examples, the signal processing module 415-*a* may also include a vector magnitude module 525. The vector magnitude module 525 may be used in aspects of correlating acceleration data received from one or more sensor units 110 with activity data of the patient. In some examples, the at-risk indicator module 420-*a* may include an activity data module 505, a posture data module 510, an at-risk module 515, and a data transmission module 520. The modules 505, 510, 515, and 520 may each be used in aspects of collecting patient movement data, determining one or more of a patient posture and a patient activity level, and determining whether an at-risk condition is satisfied by one or more of the patient posture and patient activity level. Additionally, while FIG. 5 illustrates a specific example, the functions performed by each of the modules 505, 510, 515, and 520 may be combined or implemented in one or more other modules.

The vector magnitude module 525 may further comprise an analog to digital converter (ADC, not shown). In one embodiment, at least one of the sensor units 110 may comprise an accelerometer. The accelerometer may be operable to send a signal associated with any one of detected position, velocity, and/or acceleration of the sensor unit 110 to the ADC, which may sample the analog signal output by the accelerometer and convert the analog signal into a digital acceleration signal. The ADC may then send the digital acceleration signal to the vector magnitude module 525, which may be operable to correlate the digital acceleration signal to an activity level of the patient. In some embodiments, the vector magnitude module 525 may detect acceleration signatures, patterns, magnitude, and/or direction in order to determine the type and/or intensity of the patient's physical activity. For example, the vector magnitude module 525 may compare the acceleration magnitude and/or direction to a database of activity signatures stored, for example, in a memory (not shown), and may be operable to determine that the patient is making a concerted, deliberate, and/or sustained movement in a single direction. This sustained movement may then be associated with getting out of bed or some other high-risk patient activity, as opposed to "glitch" movements indicating undirected, accidental, and/or transitory movement, such as rolling over, changing position, etc.

In some embodiments, the vector magnitude module 525 may be customizable based on the patient's age, gender, body weight, etc. The patient activity level detected by sensing module 410-*a* may be analyzed by vector magnitude module 525 to compare the calculated activity level to an activity threshold. For example, in some embodiments, the activity threshold may be equivalent to an activity level greater or equal to 0.2 VMU. The activity threshold may be any suitable threshold, however, corresponding to the user attempting to get out of bed, walking, and/or any other activity that may increase the risk of falling. Although described as separate from the one or more sensor units 110, in some embodiments apparatus 405-*a* may be a component of one or more sensor units 110 such that the signal from the accelerometer is directed within the apparatus 405-*a* component of the one or more sensor units 110 to convert the analog signal to a digital acceleration signal.

The activity data module 505 may be used to receive processed patient movement data signals received from signal processing module 415-*a* to determine whether the patient activity data is above or below the patient activity threshold 365 (of FIG. 3). As discussed above with respect to FIG. 3, the patient activity threshold 365 may comprise a predetermined threshold of patient activity, beyond which a patient is deemed to be at risk of falling.

The posture data module 510 may similarly be used to receive processed patient movement data signals received from signal processing module 415-*a* to determine whether the patient posture is above or below the patient posture threshold 370 (of FIG. 3). As discussed above with respect to FIG. 3, the patient posture threshold 370 may be a patient inclination above 0 degrees which may indicate an increased risk of falling. For example, the patient posture threshold may be, for some patients, sitting up from a reclined or supine position, to 90 degrees. As previously discussed, both patient posture thresholds and patient activity thresholds may vary based on individual patient physiological factors.

The at-risk module 515 may be used to determine, based on at least one of the determinations of activity data module 505 and posture data module 510, whether the patient is at risk of falling. Upon determination by at-risk module 515 that the patient is at-risk, the data transmission module 520 may transmit an alert instruction, via transceiver module 425-*a*, to the patient and/or a caregiver, indicating that the patient is at an increased risk of falling.

Figure 6:
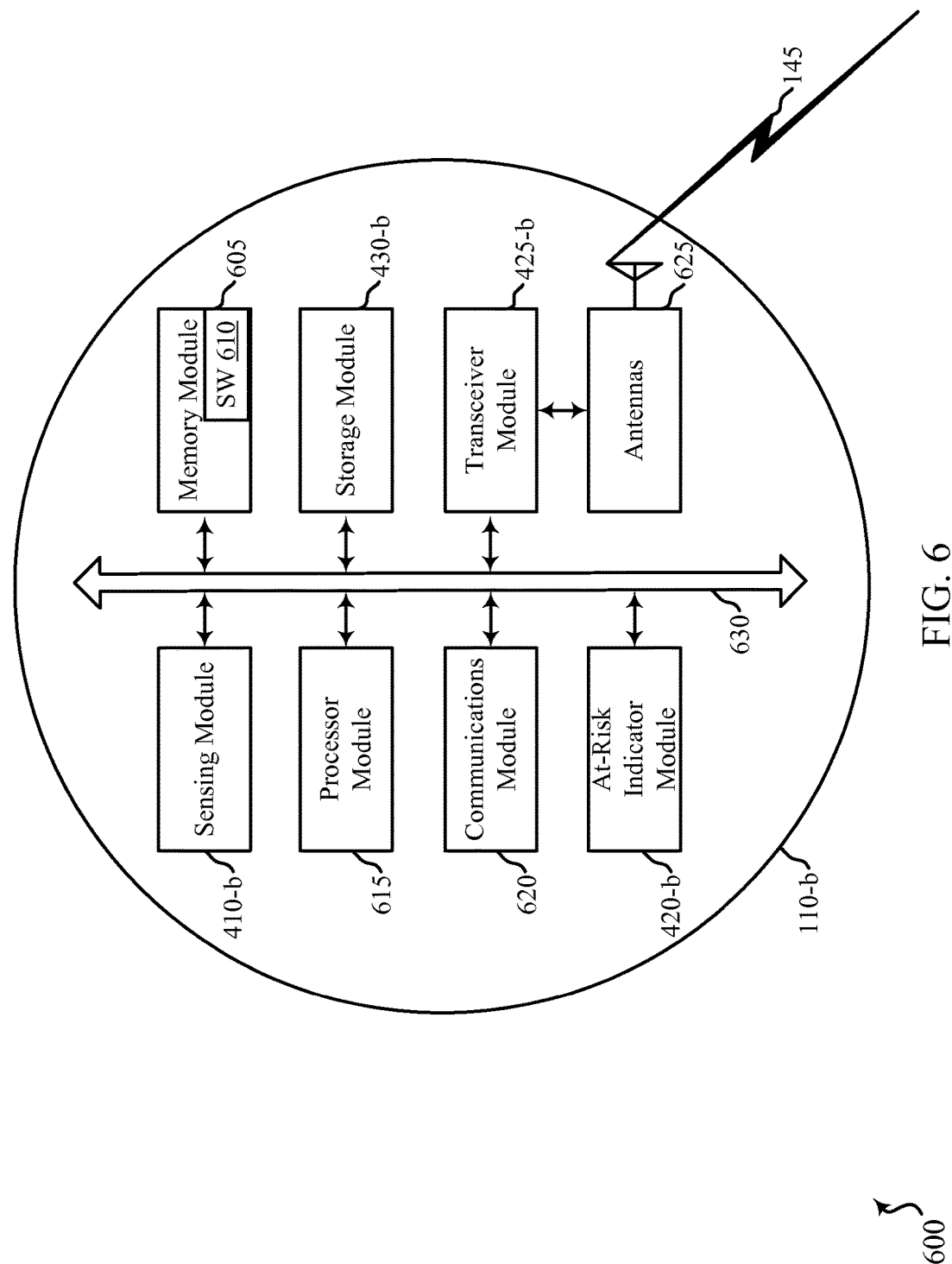
FIG. 6 is a block diagram of an example of a sensing apparatus for receiving physiological data and activity data in accordance with various embodiments.

FIG. 6 shows a block diagram 600 of a sensor unit 110-*b* for use in remote patient movement monitoring, in accordance with various aspects of the present disclosure. The sensor unit 110-*b* may have various configurations. The sensor unit 110-*b* may, in some examples, have an internal power supply (not shown), such as a small battery, to facilitate mobile operation. In some examples, the sensor unit 110-*b* may be an example of one or more aspects of one of the sensor units 110 and/or apparatus 405 described with reference to FIGS. 1, 2, 4, and/or 5. The sensor unit 110-*b* may be configured to implement at least some of the features and functions described with reference to FIGS. 1-5.

The sensor unit 110-*b*, which may include one or more aspects of apparatus 405 (as described in FIGS. 4 and/or 5) may include a sensing module 410-*b*, a processor module 615, a memory module 605, a communications module 620, at least one transceiver module 425-*b*, at least one antenna (represented by antennas 625), a storage module 430-*b*, and/or an at-risk indicator module 420-*b*. Each of these components may be in communication with each other, directly or indirectly, over one or more buses 630. The sensing module 410-*b*, the at-risk indicator module 420-*b*, the transceiver module 425-*b*, and the storage module 430-*b* may be examples of the sensing modules 410, the at-risk indicator modules 420, the transceiver modules 425, and the storage modules 430, respectively, of FIG. 4 or 5.

The memory module 605 may include RAM or ROM. The memory module 605 may store computer-readable, computer-executable software (SW) code 610 containing instructions that are configured to, when executed, cause the processor module 615 to perform various functions described herein for communicating, for example, at-risk status. Alternatively, the software code 610 may not be directly executable by the processor module 615, but may be configured to cause the sensor unit 110-*b* (e.g., when compiled and executed) to perform various of the functions described herein.

The processor module 615 may include an intelligent hardware device, e.g., a central processing unit (CPU), a microcontroller, an ASIC, etc. The processor module 615 may process information received through the transceiver module 425-*b* or information to be sent to the transceiver module 425-*b* for transmission through the antenna 625. The processor module 615 may handle, alone or in connection with the at-risk indicator module 420-*b*, various aspects of signal processing as well as determining and transmitting at-risk status indicators.

The transceiver module 425-*b* may include a modem configured to modulate packets and provide the modulated packets to the antennas 625 for transmission, and to demodulate packets received from the antennas 625. The transceiver module 425-*b* may, in some examples, be implemented as one or more transmitter modules and one or more separate receiver modules. The transceiver module 425-*b* may support at-risk status-related communications. The transceiver module 425-*b* may be configured to communicate bi-directionally, via the antennas 625 and communication link 145, with, for example, local computing devices 115, 120 and/or the remote computing device 140 (via network 125 and server 130 of FIG. 1). Communications through the transceiver module 425-*b* may be coordinated, at least in part, by the communications module 620. While the sensor unit 110-*b* may include a single antenna 625, there may be embodiments in which the sensor unit 110-*b* may include multiple antennas 625.

The at-risk indicator module 420-*b* may be configured to perform or control some or all of the features or functions described with reference to FIGS. 4 and/or 5 related to at-risk status indicator generation and transmission. For example, the at-risk indicator module 420-*b* may be configured to monitor the patient posture data and patient activity data sensed by the sensing module 410-*b*. In some examples, the at-risk indicator module 420-*b* may determine that the patient is at risk of falling based, at least in part, on one or more of the patient posture data and patient activity level data. The at-risk indicator module 420-*b* may determine that an alert should be triggered, based on at least one of the monitored patient posture data and patient activity data, and the respective determined thresholds. The at-risk status and corresponding alert instructions may be transmitted to either a local computing device 115, 120 or a remote computing device 140. The at-risk indicator module 420-*b*, or portions of it, may include a processor, or some or all of the functions of the at-risk indicator module 420-*b* may be performed by the processor module 615 or in connection with the processor module 615. Additionally, the at-risk indicator module 420-*b*, or portions of it, may include a memory, or some or all of the functions of the at-risk indicator module 420-*b* may use the memory module 605 or be used in connection with the memory module 605.

Figure 7:
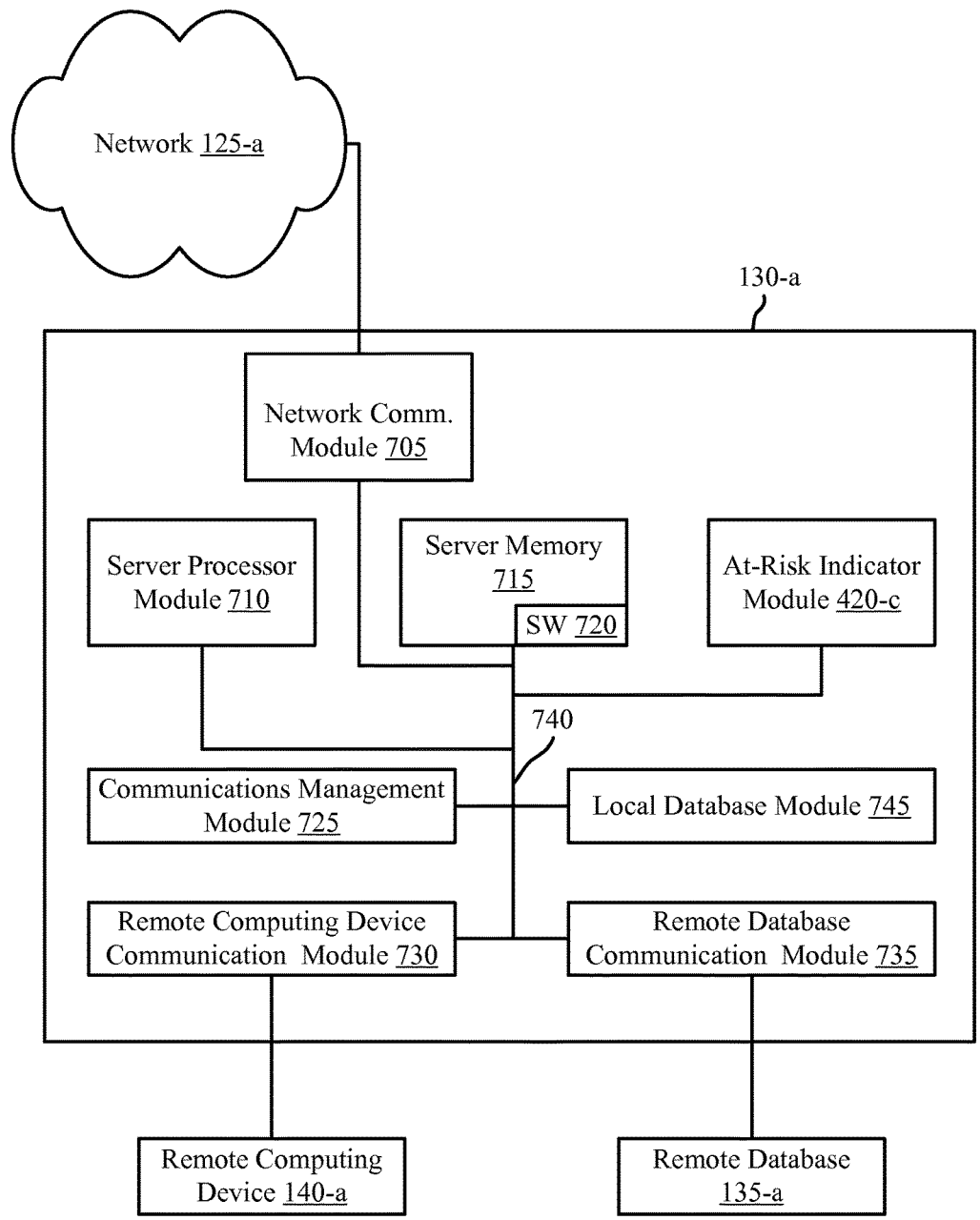
FIG. 7 is a block diagram of an example of a server for determining at-risk status in accordance with various embodiments.

FIG. 7 shows a block diagram 700 of a server 130-*a* for use in determining an at-risk status of a patient, in accordance with various aspects of the present disclosure. In some examples, the server 130-*a* may be an example of aspects of the server 130 described with reference to FIG. 1. In other examples, the server 130-*a* may be implemented in either the local computing devices 115, 120 or the remote computing device 140 of FIG. 1. The server 130-*a* may be configured to implement or facilitate at least some of the features and functions described with reference to the server 130, the local computing devices 115, 120 and/or the remote computing device 140 of FIG. 1.

The server 130-*a* may include a server processor module 710, a server memory module 715, a local database module 745, and/or a communications management module 725. The server 130-*a* may also include one or more of a network communication module 705, a remote computing device communication module 730, and/or a remote database communication module 735. Each of these components may be in communication with each other, directly or indirectly, over one or more buses 740.

The server memory module 715 may include RAM and/or ROM. The server memory module 715 may store computer-readable, computer-executable code (SW) 720 containing instructions that are configured to, when executed, cause the server processor module 710 to perform various functions described herein related to alerting of a patient at-risk status. Alternatively, the code 720 may not be directly executable by the server processor module 710 but may be configured to cause the server 130-*a* (e.g., when compiled and executed) to perform various of the functions described herein.

The server processor module 710 may include an intelligent hardware device, e.g., a CPU, a microcontroller, an ASIC, etc. The server processor module 710 may process information received through the one or more communication modules 705, 730, 735. The server processor module 710 may also process information to be sent to the one or more communication modules 705, 730, 735 for transmission. Communications received at or transmitted from the network communication module 705 may be received from or transmitted to sensor units 110 or local computing devices 115, 120 via network 125-*a*, which may be an example of the network 125 described in relation to FIG. 1. Communications received at or transmitted from the remote computing device communication module 730 may be received from or transmitted to remote computing device 140-*a*, which may be an example of the remote computing device 140 described in relation to FIG. 1. Communications received at or transmitted from the remote database communication module 735 may be received from or transmitted to remote database 135-*a*, which may be an example of the remote database 135 described in relation to FIG. 1. Additionally, a local database may be accessed and stored at the server 130-*a*. The local database module 745 may be used to access and manage the local database, which may include data received from the sensor units 110, the local computing devices 115, 120 or the remote computing devices 140 (of FIG. 1).

The server 130-*a* may also include an at-risk indicator module 420-*c*, which may be an example of the at-risk indicator module 420 of apparatus 405 described in relation to FIGS. 4, 5 and/or 6. The at-risk indicator module 420-*c* may perform some or all of the features and functions described in relation to the at-risk indicator module 420, including selecting and obtaining from either the local database module 745 or the remote database 125-*a* data corresponding to the patient posture data and patient activity data, determining whether the patient posture data and/or the activity data meets or exceeds the patient posture threshold and/or the patient activity threshold, respectively, determining on the basis of this determination whether the patient is at risk of falling, and issuing an alert based, at least in part, on the determination that the at-risk condition is satisfied.

Figure 8:
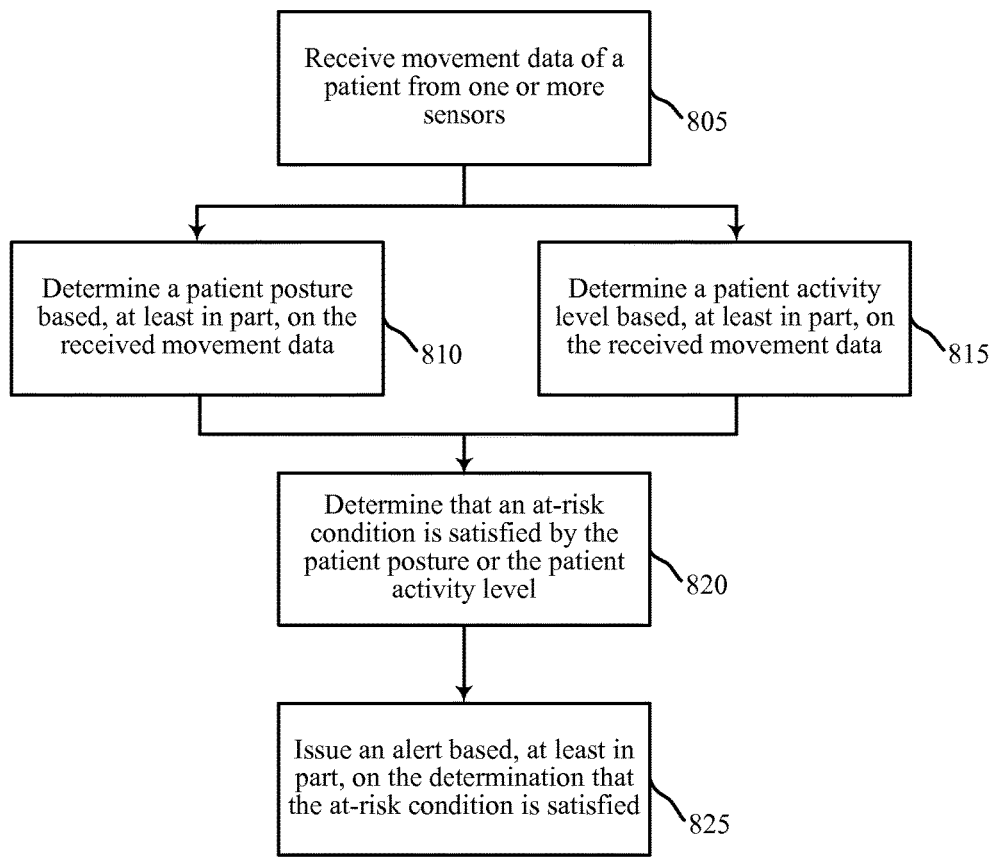
FIGS. 8 and 9 are flowcharts of various methods for determining at-risk status in accordance with various embodiments.

FIG. 8 is a flow chart illustrating an example of a method 800 of remote patient movement monitoring, in accordance with various aspects of the present disclosure. For clarity, the method 800 is described below with reference to aspects of one or more of the local computing devices 115, 120, remote computing device 140, and/or server 130 described with reference to FIGS. 1, 2, 6, and/or 7, or aspects of one or more of the apparatus 405 described with reference to FIGS. 4 and/or 5. In some examples, a local computing device, remote computing device or server such as one of the local computing devices 115, 120, remote computing device 140, server 130 and/or an apparatus such as one of the apparatuses 405 may execute one or more sets of codes to control the functional elements of the local computing device, remote computing device, server or apparatus to perform the functions described below. In alternate embodiments, method 800 may be carried out at one or more sensor units 110.

At block 805, the method 800 may include receiving movement data of a patient from one or more sensors. As discussed above, patient movement data may comprise acceleration data, position data, posture data, etc. The one or more sensors for receiving acceleration data may be the same one or more sensors for receiving posture data, or may be separate sensors.

At block 810, the method 800 may include determining a patient posture based, at least in part, on the received movement data. For example, as previously discussed with respect to FIG. 5, acceleration data received from one or more sensors may be used to calculate the angle of an accelerometer, and by extension of the patient, with respect to a horizontal surface. The determined patient posture may be, for example, supine, seated, or standing.

In some embodiments, the method 800 may proceed from block 805 to block 810, such that only patient posture is determined. In other embodiments, the method 800 may proceed from block 805 to block 815, in which the method 800 may include determining a patient activity level based, at least in part, on the received movement data. For example, as previously discussed with respect to FIG. 5, a vector magnitude module may calculate a level of patient activity based, at least in part, on received acceleration data. On the basis of this calculated patient activity level, a corresponding patient activity indicating sustained, deliberate movement may be determined. In still other embodiments, the method 800 may proceed from block 805 to blocks 810 and 815 concurrently, such that both patient posture and patient activity level are both determined based, at least in part, on the received movement data.

At block 820, the method 800 may include determining that an at-risk condition is satisfied by the patient posture or the patient activity level. As previously discussed, for example with respect to FIG. 3, an at-risk patient condition may be determined based, at least in part, on comparing the patient posture and/or the patient activity level to a predetermined patient posture threshold and/or patient activity threshold, respectively. For example, where a patient has sustained a measured acceleration beyond 0.2 VMU, it may be determined that the patient is at risk for falling based, at least in part, on deliberate movement. Similarly, where a patient has sat up to a seated position, where he is at an angle beyond 45 degrees with respect to a horizontal surface, it may be determined that the patient is at an increased risk for falling.

At block 825, the method 800 may include issuing an alert based, at least in part, on the determination that the at-risk condition is satisfied. Thus, where it has been determined at block 820 that the patient posture has met or exceeded the predetermined patient posture threshold, and/or where it has been determined at block 820 that the patient activity level has met or exceeded the predetermined patient activity threshold, it may be determined that the patient is at increased risk of falling, and therefore an alert may be communicated to the patient and/or caregiver. For example, the alert may be communicated to a nurses' station in the form of an auditory or visual alert, or may be additionally or alternatively issued as an auditory alert from the sensor unit worn by or attached to the patient.

In some embodiments, the operations at blocks 805, 810, 815, 820 or 825 may be performed using the at-risk indicator module 420 described with reference to FIGS. 4, 5, and/or 6. Nevertheless, it should be noted that the method 800 is just one implementation and that the operations of the method 800 may be rearranged or otherwise modified such that other implementations are possible.

Figure 9:
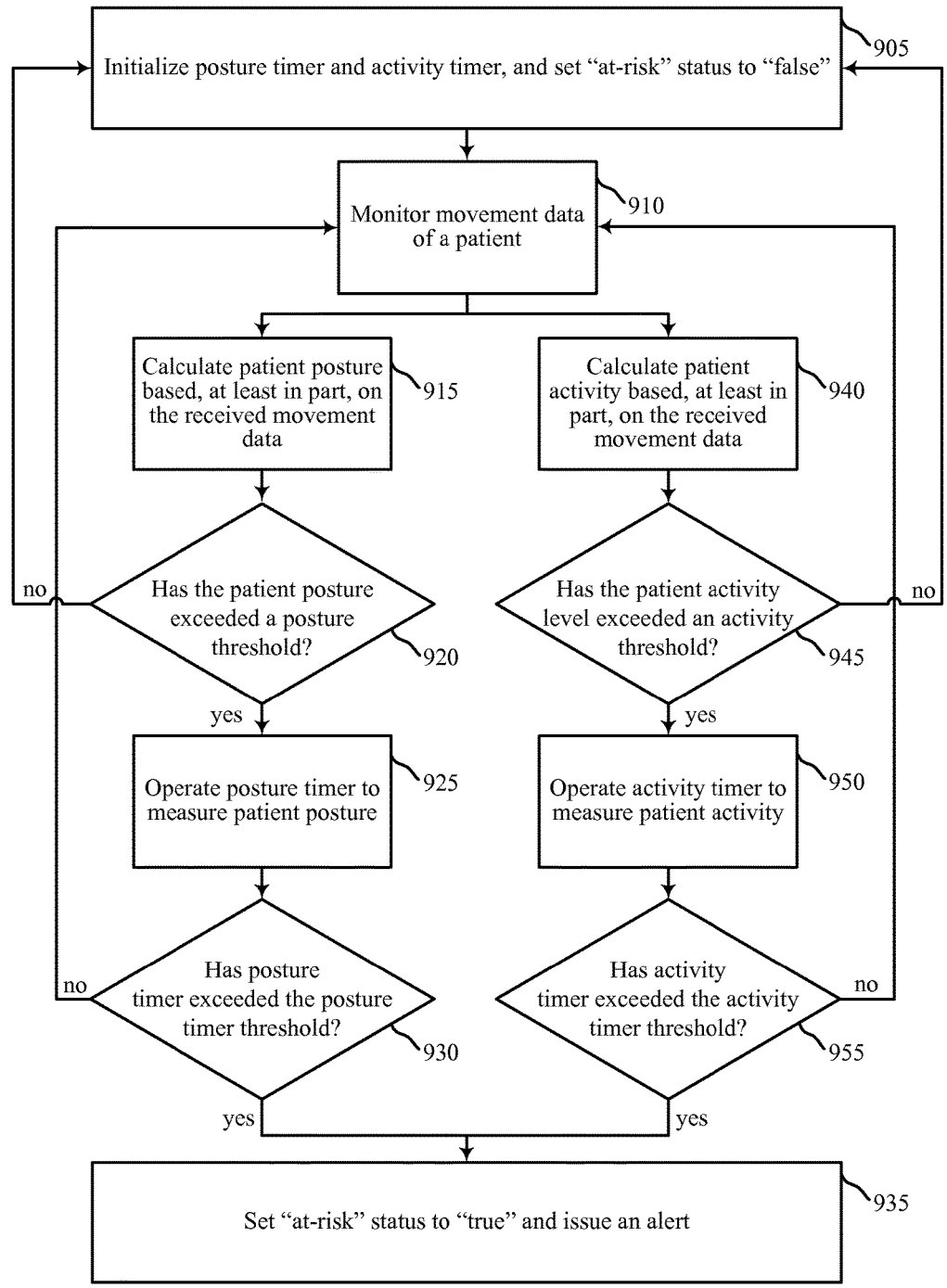

FIG. 9 is a flow chart illustrating an example of a method 900 for determining whether an at-risk condition is met on the basis of the collecting of patient posture and activity data, as well as the use of posture timers and activity timers, in accordance with various aspects of the present disclosure. For clarity, the method 900 is described below with reference to aspects of one or more of the local computing devices 115, 120, remote computing device 140, and/or server 130 described with reference to FIGS. 1 and/or 7, or aspects of one or more of the apparatus 405 described with reference to FIGS. 4 and/or 5. In alternative embodiments, method 900 may be performed at one or more of the sensor units 110. In some examples, a sensor unit, a local computing device, remote computing device or server such as one of the sensor units 110, local computing devices 115, 120, remote computing device 140, server 130 (of FIGS. 1, 2, 6 and/or 7, for example) and/or an apparatus such as one of the apparatuses 405 (of FIGS. 4 and/or 5) may execute one or more sets of codes to control the functional elements of the local computing device, remote computing device, server or apparatus to perform the functions described below.

The method 900 may be used, for example, to monitor movement data of a patient to determine whether the patient's posture and/or activity level has met or surpassed a predetermined patient posture threshold and/or patient activity threshold, respectively. Where it has been determined that the patient is at-risk based, at least in part, on the determined posture and/or activity level, and where the patient has maintained this at-risk status beyond a predetermined period of time, an alert may be issued to notify the patient and/or a caregiver that the patient is at risk of falling. In some embodiments, the patient may be monitored in a hospital, a hospice or other healthcare related facility. In other embodiments, the patient may be monitored at home and the alert may be provided to a caregiver at the patient's home.

As shown in FIG. 9, at step 905, the method 900 may include initializing a posture timer and an activity timer, and setting an "at-risk" status to "false." As described above with reference to FIG. 3, in some embodiments, the at-risk condition is set to "true," and an alert 350, 360 is issued, when either the patient activity level or the patient posture, or both, have exceeded the patient activity threshold and patient posture threshold, respectively, and have maintained this at-risk status for a predetermined period of time. The predetermined period of time may be measured by an at-risk timer window 345-$a$-1, 345-$a$-2, 345-$a$-3 of any suitable length to distinguish minor movements from concerted efforts to exit the bed, for example 3 seconds, 5 seconds, 10 seconds, etc. Individual at-risk timer window durations may be adjusted based on individual patients' health and fitness levels.

At step 910, the method 900 may include monitoring movement data of a patient. For example, the local computing devices 115, 120, remote computing device 140 and/or server 130 shown and described above with reference to FIG. 1 may receive one or more acceleration data streams from the sensor units 110 and/or the local computing devices 115, 120 and may store the received data, for example, in a database. Each of the received data streams may be associated with a different patient movement parameter and may be received from one or more sensor units 110. In some embodiments, patient movement data collected by the one or more sensor units 110 may remain at the one or more sensor units 110 for local processing, without the use of local computing devices 115, 120 or remote computing device 140.

At step 915, the method 900 may include calculating a patient posture based, at least in part, on the received movement data. As previously discussed with respect to FIGS. 4-5, a patient posture may be determined based on calculating an angle of the sensor unit above a horizontal plane, where the angle of the sensor unit may correlate to the angle of the patient. For example, a sensor unit detected at an angle of 45 degrees may indicate a patient who is reclined at an angle 45 degrees above the horizontal plane, while a sensor unit detected to be at an angle of 90 degrees may indicate a patient who is sitting upright or standing.

At step 920, the method 900 may include determining whether the patient posture has exceeded a posture threshold. The predetermined posture threshold may vary according to individual patient physiological parameters, and may be selected to indicate a degree of inclination above 0 degrees that is associated with an increased risk of falling for the patient. Thus, for some patients, the posture threshold may be 50 degrees above the horizontal surface of the bed, while for other, less stable patients, the posture threshold may be 30 degrees above the horizontal surface. Where it is determined at step 920 that the patient posture has not exceeded the predetermined posture threshold, the method 900 may return to step 905, at which the posture timer and activity timer may be re-initialized, and the "at-risk" status may be set to false. Alternatively, where it is determined at step 920 that the patient posture has met or exceeded the predetermined posture threshold, it may be determined that the patient is at an increased risk of falling, and the method 900 may proceed to step 925.

At step 925, the method 900 may include operating a posture timer to measure the period of time spent by the patient at the posture determined at steps 915 and 920 to constitute an increased risk of falling. The posture timer may be operated for a predetermined period of time to determine whether the patient has remained in the detected posture beyond a "glitch" period. In other words, the posture timer may require the patient to have made a concerted, continued effort to exit the bed in order to determine that the patient is at risk of falling. Where a patient has merely inclined his position momentarily, for example to reach for an object on a bedside table or to scratch an itch, but shortly thereafter returns to a reclined position, that movement may be disregarded as temporary and not contributing to an "at-risk" status.

At step 930, the method 900 may include determining whether the posture timer has exceeded the posture timer threshold. Thus, where the patient has maintained the posture that has been determined to represent a heightened risk of falling for a period exceeding the predetermined posture timer threshold, it may be determined that the patient is making a purposeful, continuous effort to leave his bed. Accordingly, at step 935, the "at-risk" status may be set to "true," and an alert may be issued to notify the patient and/or a caregiver that the patient is at risk of falling. Alternatively, where it is determined at step 930 that the patient maintained his heightened risk posture only momentarily, and has returned to a low-risk posture prior to the posture timer threshold, the method 900 may return to step 910, at which patient movement data may continue to be monitored.

In some embodiments, patient posture may be monitored individually to determine whether a patient is at risk of falling. In other embodiments, patient activity level may be monitored individually to determine whether the patient is at risk of falling. In still other embodiments, the patient posture and patient activity level may be monitored concurrently to determine whether the patient is at risk of falling. Accordingly, at step 910, the method 900 may proceed to either step 915 to calculate patient posture, or to step 940 to calculate patient activity level, or to both.

At step 940, the method 900 may include calculating patient activity based, at least in part, on the received movement data. As previously discussed with respect to FIG. 5, a vector magnitude module 525 may collect patient movement data monitored by the one or more sensor units, and derive position, velocity, and/or acceleration of the sensor units accordingly. A derived digital acceleration signal may then be correlated to an activity level of the patient, where the vector magnitude module may use the activity level to determine the type and/or intensity of the patient physical activity.

At step 945, the method 900 may include determining whether the patient activity level has exceeded an activity threshold. In this way, minor activities, such as reaching for an object or readjusting position in bed, may be disregarded as not contributing to a heightened risk of falling. Where it is determined that the patient activity level has been a "glitch," the method 900 may return to step 905, to initialize the posture timer and activity timer, and set the "at-risk" status to "false." Alternatively, where it is determined at step 945 that the patient activity level has exceeded the activity threshold, which may be, in some examples, 0.2 VMU, the method 900 may proceed to step 950.

At step 950, the method 900 may include operating an activity timer to measure patient activity. As with the posture timer at step 925, the activity timer may be utilized to differentiate between brief, negligible patient movements, and concerted, continuous patient efforts to leave the bed.

At step 955, it may accordingly be determined whether the patient has maintained a level of patient activity indicating a heightened risk of falling for a period of time meeting or exceeding the activity timer threshold. The activity timer threshold may be predetermined based on individual patient parameters. For example, where a patient is in ill health and has very little coordination, any heightened patient activity lasting more than 5 seconds may be determined to be risky, while for other, more coordinated patients, the heightened activity may need to last beyond 10 seconds or more to be deemed dangerous. Where, at step 955, it is determined that the patient activity timer has not exceeded the predetermined activity timer threshold, the method 900 may return to step 910, to continue to monitor movement data of the patient. Alternatively, where it is determined that the activity timer has met or exceeded the activity timer threshold, the method 900 may proceed to step 935.

At step 935, the method may comprise setting the "at-risk" status to "true," and issuing an alert to notify the patient and/or caregiver that the patient is at risk of falling.

The above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, a FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration. A processor may in some cases be in electronic communication with a memory, where the memory stores instructions that are executable by the processor.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items indicates a disjunctive list such that, for example, a list of "at least one of A, B, or C" means A or B or C or AB or AC or BC or ABC (i.e., A and B and C).

A computer program product or computer-readable medium both include a computer-readable storage medium and communication medium, including any mediums that facilitate transfer of a computer program from one place to another. A storage medium may be any medium that may be accessed by a general purpose or special purpose computer. By way of example, and not limitation, a computer-readable medium may comprise RAM, ROM, EEPROM, CD-ROM or other optical disk storage, magnetic disk storage or other magnetic storage devices, or any other medium that may be used to carry or store desired computer-readable program code in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote light source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and Blu-ray disc where disks usually reproduce data magnetically, while discs generally reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. A method of issuing an alert, comprising:
   receiving movement data of a patient from one or more sensors;
   determining a patient posture and a patient activity level based, at least in part, on the received movement data;
   determining that an at-risk condition is satisfied by the patient posture or the patient activity level exceeding a respective patient posture or the patient activity level threshold for a predetermined period of time;
   operating a timer to measure the period of time for which at least one of the patient posture or the patient activity level satisfies the at-risk determined condition; and
   issuing an alert based at least in part on the determination that the at-risk condition is satisfied and that the period of time has met or surpassed a predetermined timer threshold.

2. The method of claim 1, wherein receiving movement data comprises:
   receiving orientation, position, velocity, posture, or acceleration data from the one or more sensors.

3. The method of claim 1, wherein the timer comprises a posture timer, the method further comprising:
   operating the posture timer to measure the patient posture for the predetermined period of time during which the at-risk condition is satisfied; and
   issuing the alert when the posture timer meets or surpasses a predetermined posture timer threshold.

4. The method of claim 3, further comprising:
   re-initializing the posture timer when the patient posture does not satisfy the at-risk threshold.

5. The method of claim 3, further comprising:
   setting the predetermined posture timer threshold based, at least in part, on patient physiological factors.

6. The method of claim 1, wherein the timer comprises an activity timer, the method further comprising:
   operating the activity timer to measure the patient activity level for the predetermined period of time during which the at-risk condition is satisfied; and
   issuing the alert when the activity timer meets or surpasses a predetermined activity timer threshold.

7. The method of claim 6, further comprising:
   re-initializing the activity timer when the patient activity level does not satisfy the at-risk threshold.

8. The method of claim 6, further comprising:
   setting the predetermined activity timer threshold based, at least in part, on patient physiological factors.

9. The method of claim 1, further comprising:
   transmitting the issued alert to a monitoring station.

10. The method of claim 1, wherein determining that the at-risk condition is satisfied by the patient activity level comprises:
correlating the patient movement data received with a vector magnitude (VMU).

11. The method of claim 10, further comprising:
determining that the at-risk condition is satisfied when the VMU reaches or surpasses a predetermined VMU threshold based, at least in part, on the activity level of the patient.

12. A remote patient monitoring device, comprising:
a transceiver configured to receive movement data of a patient from one or more sensors; and
a processor configured to:
determine a patient posture and a patient activity level based, at least in part, on the received movement data;
determine that an at-risk condition is satisfied by the patient posture or the patient activity level exceeding a respective patient posture or the patient activity level threshold for a predetermined period of time;
operate a timer to measure a period of time for which at least one of the patient posture or the patient activity level satisfies the at-risk determined condition; and
issue an alert based at least in part on the determination that the at-risk condition is satisfied and that the period of time has met or surpassed a predetermined timer threshold.

13. The device of claim 12, wherein the timer comprises a posture timer,
the posture timer configured to:
operate to measure the patient posture for the predetermined period of time during which the at-risk condition is satisfied; and
issue the alert when the posture timer meets or surpasses a predetermined posture timer threshold.

14. The device of claim 13, wherein the processor is further configured to:
re-initialize the posture timer when the patient posture does not satisfy the at-risk threshold.

15. The device of claim 13, wherein the processor is further configured to:
set the predetermined posture timer threshold based, at least in part, on patient physiological factors.

16. The device of claim 12, wherein the timer comprises an activity timer,
the activity timer configured to:
operate to measure the patient activity level for the predetermined period of time during which the at-risk condition is satisfied; and
issue the alert when the activity timer meets or surpasses a predetermined activity timer threshold.

17. The device of claim 16, wherein the processor is further configured to:
re-initialize the activity timer when the patient activity level does not satisfy the at-risk threshold.

18. The device of claim 16, wherein the processor is further configured to:
set the predetermined activity timer duration based, at least in part, on patient physiological factors.

19. The device of claim 12, wherein the processor is further configured to:
correlate the patient movement data received with a vector magnitude (VMU); and
determine that the at-risk condition is satisfied when the VMU reaches or surpasses a predetermined VMU threshold based, at least in part, on the activity level of the patient.

20. A non-transitory computer-readable medium storing computer-executable code, the code executable by a processor to:
receive movement data of a patient from one or more sensors;
determine a patient posture and a patient activity level based, at least in part, on the received movement data;
determine that an at-risk condition is satisfied by the patient posture or the patient activity level exceeding a respective patient posture or the patient activity level threshold for a predetermined period of time;
operate a timer to measure a period of time for which at least one of the patient posture or the patient activity satisfies the at-risk determined condition; and
issue an alert based at least in part on the determination that the at-risk condition is satisfied and that the period of time has met or surpassed a predetermined timer threshold.

* * * * *